US012805768B2

(12) United States Patent
Yang

(10) Patent No.: US 12,805,768 B2
(45) Date of Patent: Nov. 24, 2026

(54) ANALYTE DETECTION DEVICE WITH BATTERY AND SHELL INTEGRATED

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 299 days.

(21) Appl. No.: 18/694,421

(22) PCT Filed: Dec. 8, 2021

(86) PCT No.: PCT/CN2021/136529
§ 371 (c)(1),
(2) Date: Mar. 22, 2024

(87) PCT Pub. No.: WO2023/045100
PCT Pub. Date: Mar. 30, 2023

(65) Prior Publication Data

US 2024/0389896 A1 Nov. 28, 2024

(30) Foreign Application Priority Data

Sep. 27, 2021 (WO) ................ PCT/CN2021/120856

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0002* (2013.01); *A61B 5/145* (2013.01);
(Continued)

(58) Field of Classification Search
CPC ... A61B 5/0002; A61B 5/145; A61B 5/14503; A61B 5/14532; A61B 5/14546;
(Continued)

(56) References Cited

U.S. PATENT DOCUMENTS

2010/0294661 A1 11/2010 Fitzgerald et al.
2016/0045145 A1* 2/2016 Brister ................ A61B 5/1495 600/365
(Continued)

FOREIGN PATENT DOCUMENTS

CN 102569680 A * 7/2012
CN 112294309 A * 2/2021 .......... A61B 5/6849
WO 2021179129 9/2021

OTHER PUBLICATIONS

"International Search Report (Form PCT/ISA/210) of PCT/CN2021/136529," mailed on Jul. 1, 2022, pp. 1-2.

*Primary Examiner* — Severo Antonio P Lopez
(74) *Attorney, Agent, or Firm* — JCIP GLOBAL INC.

(57) ABSTRACT

An analyte detection device includes an outer shell, a circuit board and a battery cavity. The battery cavity includes a cavity shell, a diaphragm, an electrolyte, an anode plate, a cathode plate and a conductive strip, an electrolyte isolation layer is also arranged inside the cavity shell, an upper cover shell of the cavity shell is integrated with the circuit board. The shape and size of the battery cavity can be optimized according to the miniaturization design requirements of the analyte detection device to improve user experience.

14 Claims, 9 Drawing Sheets

(51) Int. Cl.

| | |
|---|---|
| ***A61B 5/1468*** | (2006.01) |
| ***A61B 5/1473*** | (2006.01) |
| ***A61B 5/1486*** | (2006.01) |
| ***A61B 5/1495*** | (2006.01) |
| ***B01L 3/00*** | (2006.01) |
| ***C12Q 1/00*** | (2006.01) |
| ***G16H 40/67*** | (2018.01) |

(52) U.S. Cl.

CPC ...... *A61B 5/14503* (2013.01); *A61B 5/14546* (2013.01); *A61B 5/1473* (2013.01); *A61B 5/1486* (2013.01); *A61B 5/14865* (2013.01); *A61B 5/1495* (2013.01); *A61B 5/6835* (2013.01); *A61B 5/6847* (2013.01); *A61B 5/6848* (2013.01); *A61B 5/6849* (2013.01); *A61B 5/7264* (2013.01); *A61B 5/7405* (2013.01); *A61B 5/742* (2013.01); *A61B 5/7455* (2013.01); *A61B 5/746* (2013.01); *B01L 3/502715* (2013.01); *C12Q 1/006* (2013.01); *G16H 40/67* (2018.01); *A61B 5/1468* (2013.01); *A61B 2560/0209* (2013.01); *A61B 2560/0214* (2013.01); *A61B 2560/0223* (2013.01); *A61B 2560/0228* (2013.01); *A61B 2560/0238* (2013.01); *A61B 2560/0443* (2013.01); *A61B 2560/045* (2013.01); *A61B 2560/0462* (2013.01); *B01L 2200/0689* (2013.01); *B01L 2300/023* (2013.01); *B01L 2300/0645* (2013.01); *B01L 2300/0832* (2013.01); *B01L 2300/088* (2013.01); *B01L 2300/12* (2013.01)

(58) Field of Classification Search

CPC ... A61B 5/1459; A61B 5/1473; A61B 5/1486; A61B 5/14865; A61B 5/1495; A61B 5/6835; A61B 5/6847; A61B 5/6848; A61B 5/6849; A61B 5/7264; A61B 5/7405; A61B 5/742; A61B 5/7455; A61B 5/746; A61B 2560/0209; A61B 2560/0214; A61B 2560/0223; A61B 2560/0228; A61B 2560/0238; A61B 2560/0443; A61B 2560/045; A61B 2560/0462; B01L 3/502715; B01L 2200/0689; B01L 2300/023; B01L 2300/0645; B01L 2300/0832; B01L 2300/088; B01L 2300/12; C12Q 1/006; G16H 40/67; H01Q 1/24; H01Q 1/36; Y02D 30/70; Y02E 60/10

See application file for complete search history.

(56) References Cited

U.S. PATENT DOCUMENTS

| | | | | |
|---|---|---|---|---|
| 2016/0242696 | A1 | 8/2016 | Bolognia | |
| 2017/0055896 | A1* | 3/2017 | Al-Ali | A61B 5/01 |
| 2017/0069940 | A1 | 3/2017 | Goldstein et al. | |
| 2017/0290546 | A1* | 10/2017 | Antonio | A61B 5/14865 |
| 2017/0325741 | A1 | 11/2017 | Lim et al. | |
| 2018/0309168 | A1* | 10/2018 | Liao | H01M 10/0567 |
| 2020/0015720 | A1* | 1/2020 | Peterson | A61B 5/14865 |
| 2021/0193977 | A1 | 6/2021 | Reykhert | |

* cited by examiner

ANALYTE DETECTION DEVICE WITH BATTERY AND SHELL INTEGRATED

CROSS-REFERENCE TO RELATED APPLICATION

This application is a 371 of international application of PCT application serial no. PCT/CN2021/136529, filed on Dec. 8, 2021, which claims the priority benefit of China application no. PCT/CN2021/120856, filed on Sep. 27, 2021.

TECHNICAL FIELD

The invention mainly relates to the field of medical devices, in particular to an analyte detection device with battery and shell integrated.

BACKGROUND

The pancreas in the normal human body automatically monitors the glucose level in the blood and secretes the required insulin/glucagon automatically. In diabetics, however, the pancreas does not function properly and cannot properly produce the insulin the body needs. Therefore, diabetes is a metabolic disease caused by abnormal pancreas function, and diabetes is a lifelong disease. At present, the medical technology cannot cure diabetes completely, but can only control the occurrence and development of diabetes and its complications by stabilizing blood glucose.

Diabetics need to test their blood glucose before injecting insulin into the body. Most of the current methods can continuously monitor blood glucose and send data to a remote device in real time for users to view. This method is called Continuous Glucose Monitoring (CGM). This method requires the detection device to be attached to the skin surface, and the probe carried by it is inserted into the subcutaneous tissue fluid to complete the detection.

Existing technology of analyte detection devices, power is supplied by button battery and thus the analyte detection device is subject to button battery in the shape and size, increased the difficulty of the device further miniaturization design, secondly, button battery storage capacity is limited, can't meet the job requirements of the analyte detection device for a long time.

Therefore, the existing technology is in urgent need of an analyte detection device with battery and shell integrated with smaller battery volume and larger capacity.

BRIEF SUMMARY OF THE INVENTION

The embodiment of the invention discloses an analyte detection device with battery and shell integrated, a battery cavity is arranged in the outer shell, the cavity shell comprises the upper cover shell and the lower shell, the upper cover shell is integrated with the circuit board. The diaphragm, the electrolyte, the anode plate, the cathode plate and the conductive strip are arranged in the cavity shell, the electrolyte insulation layer is also arranged in the cavity shell, to form the highly integrated analyte detection device with battery and outer shell integration, the shape and size of the analyte detection device are no longer limited by the shape and size of the button battery. After the integration of the battery and circuit board, the battery has more available space and smaller occupied volume, which can meet the design requirements of analyte detection device miniaturization.

The invention discloses an analyte detection device with battery and shell integrated, which comprises the outer shell, the outer shell is divided into the upper outer shell and the lower outer shell; The circuit board and the battery cavity are arranged inside the lower outer shell, and the sensor is arranged on the upper outer shell; A transmitter antenna is arranged on the circuit board for communication with external equipment; The battery cavity comprises the cavity shell, the diaphragm, the electrolyte, the anode plate, the cathode plate and the conductive strip. The cavity shell comprises the upper cover shell and the lower shell, the upper cover shell is integrated with the circuit board.

According to one aspect of the invention, the lower shell is integrated with the lower outer shell.

According to one aspect of the invention, the electrolyte insulation layer is arranged in the cavity shell.

According to one aspect of the invention, the electrolyte insulation layer is made of TPE or PET material.

According to one aspect of the invention, the electrolyte isolation layer is a film arranged on the inner wall of the cavity shell.

According to one aspect of the invention, the thickness of the film is 300-500 um.

According to one aspect of the invention, the electrolyte isolation layer is a closed shell independent of the cavity shell.

According to one aspect of the invention, the end A of the conductive strip is fixedly connected with the anode plate or the cathode plate, and the other end B of the conductive strip is electrically connected with the circuit board.

According to one aspect of the invention, the sealant is coated at the junction of the upper cover shell and the lower shell, the conductive strip and the lower shell.

According to one aspect of the invention, the sealant is one of hot melt adhesive and silica gel.

According to one aspect of the invention, the end B of the conductive strip is fixedly connected with the circuit board by solder or solder paste.

According to one aspect of the invention, the material of the cavity shell is PE, PP, HDPE, PVC, ABS, PMMA, PC, PPS or PU.

According to one aspect of the invention, the sensor comprises an internal part and an external part, the internal part is bent relative to the external part.

According to one aspect of the invention, the external part is tiled inside the upper outer shell and the internal part passes through the upper outer shell to the outside.

According to one aspect of the invention, the external part is electrically connected with the circuit board.

According to one aspect of the invention, the external part of the upper outer shell is provided with a sticky patch for sticking on the user's skin surface.

Compared with the prior art, the technical scheme of the invention has the following advantages: The invention discloses an analyte detection device with battery and shell integrated, the battery cavity is installed in the outer shell, the battery cavity comprises cavity shell, diaphragm, electrolyte, anode plate, cathode plate and conductive strip, the electrolyte isolation layer is also arranged inside the cavity shell, to form the structure of battery and circuit board integration, the shape and size of the analyte detector are no longer limited by the shape and size of shell of the button battery. According to the miniaturization design requirements of analyte detection devices, the shape and size of the battery cavity can be optimized to improve user experience.

Further, the structure design of battery and circuit board integration, which can make full use of space of detection device. When the volume of analyte detection device becomes smaller, more active substances can be filled in the battery cavity, therefore, compared with the button battery, the battery cavity power increases, and the endurance time of analyte detection device is increased.

Further, the upper cover shell of the battery cavity is integrated with the circuit board, the connection between the lower shell and the upper cover shell is coated with an insulating sealant, forming a good sealing environment in the cavity, which can prevent electrolyte leakage and external air from entering the cavity shell.

Further, the electrolyte insulation layer is made of TPE or PET material, which can effectively prevent corrosion of the cavity shell caused by the electrolyte.

Further, the external part of the sensor is bent relative to the internal part, the external part is tiled in the upper shell, and the internal part passes through the upper outer shell to the outside, which can reduce the height of the sensor, thus reducing the thickness of the shell, and is conducive to the miniaturization design of analyte detection device.

DETAILED DESCRIPTION

As mentioned above, the shape and size of existing analyte detection devices are limited by the shape and size of shell of button battery, which increases the difficulty of further miniaturization design of device.

In order to solve the problem, the invention provides an analyte detection device with battery and shell integrated. The battery cavity is installed in the outer shell, the battery cavity comprises the cavity shell, the diaphragm, the electrolyte, the anode plate, cathode plate and the conductive strip, the electrolyte isolation layer is also arranged inside the cavity shell, to form the structure of battery and circuit board integration, the shape and size of the analyte detection device are no longer limited by the shape and size of the shell of the button battery, and the shape and size of the battery cavity can be optimized according to the miniaturization design requirements of the analyte detection device to improve user experience.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e.g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

First Embodiment

Figure 1A:
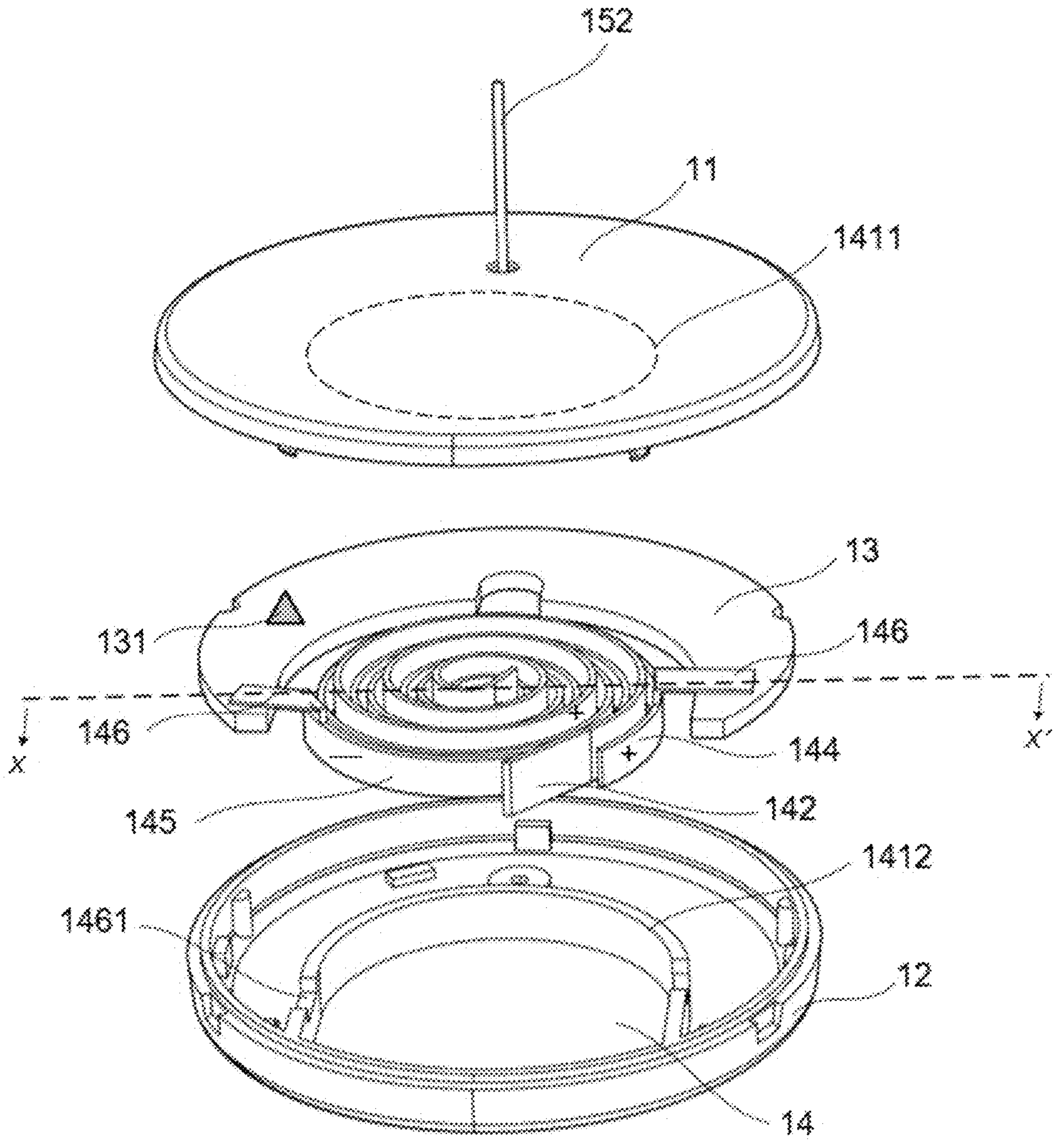
FIG. 1*a* is an explosive structure diagram of an integrated analyte detection device in a battery housing according to the first embodiment of the invention.
Figure 1B:
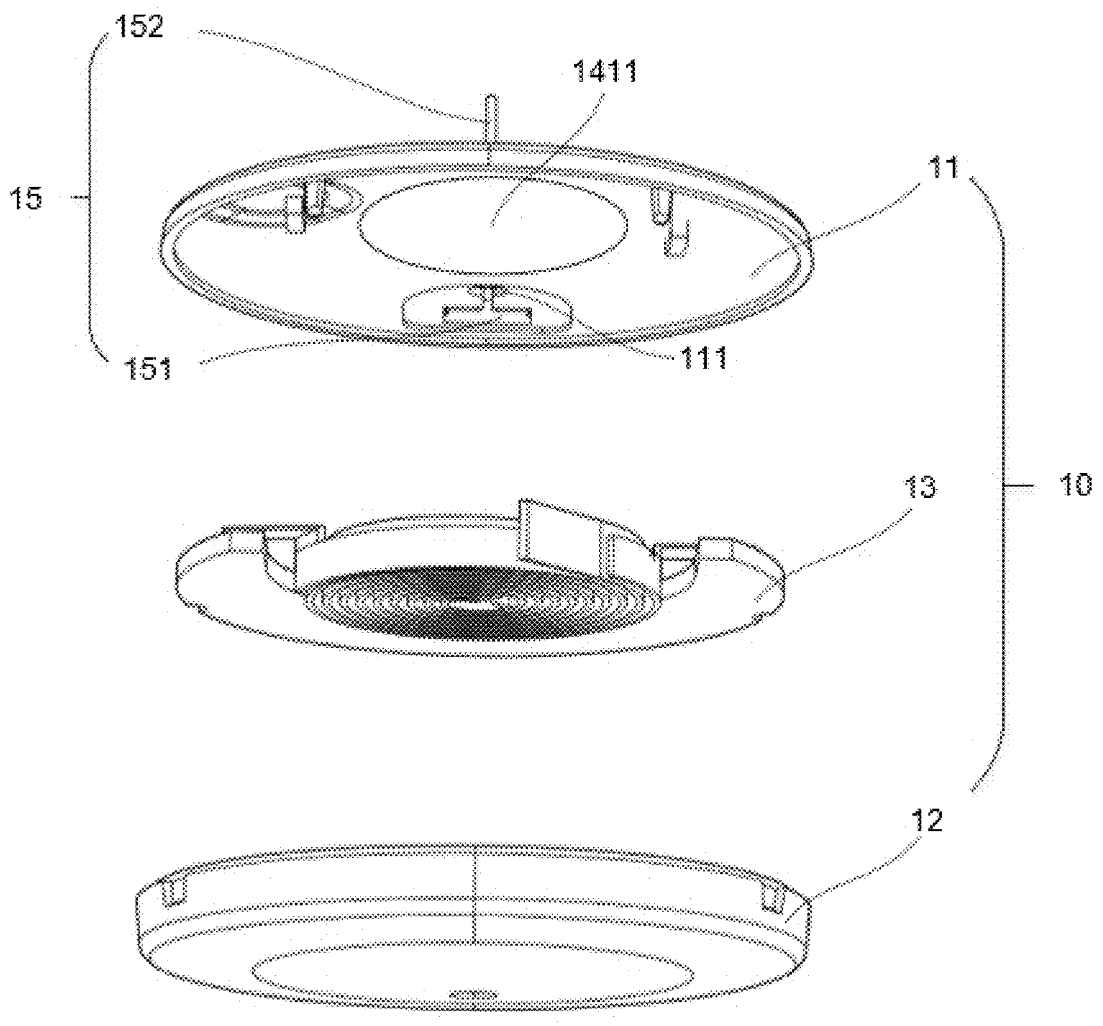
FIG. 1*b* is an explosive structure diagram of an integrated analyte detection device in the other direction according to the first embodiment of the invention.
Figure 2:
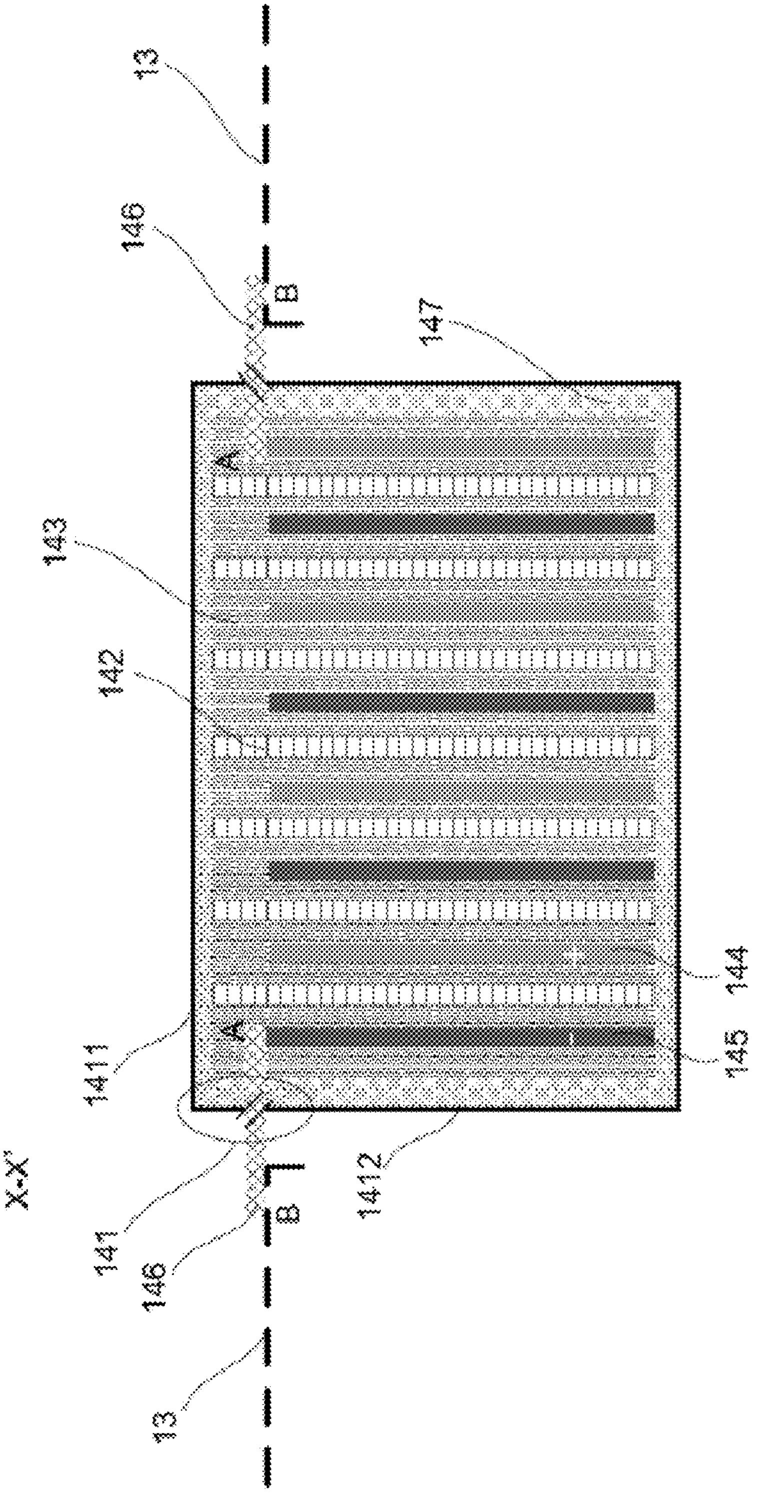
FIG. 2 is a schematic diagram of the X-X' section structure of the battery cavity according to the first embodiment of the invention.

FIG. 1*a* is the explosive structure diagram of the analyte detection device with battery and outer shell integrated in the first embodiment of the present invention. FIG. 1*b* is the explosive structure diagram of the analyte detection device with battery and outer shell integrated in the other direction in the first embodiment of the present invention. FIG. 2 is a schematic diagram of the X-X' section structure of the battery cavity in the first embodiment of the present invention.

Combine with reference FIG. 1*a*, FIG. 1*b* and FIG. 2. The detection device comprises the outer shell 10, the circuit board 13, the battery cavity 14 and the sensor 15. Outer shell 10 comprises an upper outer shell 11 and a lower outer shell 12, circuit board 13 and battery cavity 14 are arranged on the lower outer shell 12, and the sensor 15 is arranged on the upper outer shell 11.

In the embodiment of the invention, the outer shell 10 of the detection device adopts a material of PE, PP, HDPE, PVC, ABS, PMMA, PC, PPS or PU, whose low density can reduce the weight of the detection device and improve the user experience.

In an embodiment of the invention, the cavity shell 141 of battery cavity 14 comprises an upper cover shell 1411 and a lower shell 1412. The bottom of the lower shell 1412 is a part of the lower outer shell 12, the side wall of the lower shell 1412 is raised in the lower outer shell 12, and toward the upper outer shell 11, forming the structure of the lower shell 1412 and the lower outer shell 12 integration.

In the preferred embodiment of the invention, the material of the lower shell 1412 is the same as that of the lower outer shell 12, which is convenient for integrated injection molding during processing.

In an embodiment of the invention, the upper cover shell 1411 is a part of the upper outer shell 11, forming a structure of the upper cover shell 1411 and the upper outer shell 11 integration.

In the preferred embodiment of the invention, the upper cover shell 1411 has the same material as the upper and outer shell body 11, which is convenient for integrated injection molding during processing.

In an embodiment of the invention, the lower shell 1412 and the lower outer shell 12, and the upper cover shell 1411 and the upper outer shell 11 can be injection molded simultaneously or separately. For example, when the lower shell 1412 and the lower outer shell 12 are integrated in injection molding, the upper cover shell 1411 is independent of the upper outer shell 11. For example, when the upper cover shell 1411 and the upper outer shell 11 are integrated in injection molding, the lower shell 1412 is a cavity shell independent of the lower outer shell 12.

In the preferred embodiment of the invention, the lower shell 1412 and the lower outer shell 12, and the upper cover shell 1411 and the upper outer shell 11 are injection molded simultaneously integrated, which is more suitable for the miniaturization design of analyte detection device.

In the embodiment of the invention, for the upper cover shell 1411 and the lower shell 1412 made of plastic materials, such as PE (polyethylene), PP (polypropylene) and PC (polycarbonate), which are easy to be corroded by the electrolyte, it is necessary to set an electrolyte isolation layer 147 on the inner side of the upper cover shell 1411 and the lower shell 1412.

In the embodiment of the invention, the material of the electrolyte isolation layer 147 is one of TPE or PET (polyethylene terephthalate). TPE is a thermoplastic elastomer material with strong processability. PET can be used as the container of electrolyte, which can effectively isolate the corrosion of electrolyte to the cavity shell and circuit devices.

In embodiments of the present invention, the electrolyte isolation layer 147 may be either a film coated on the inner side of the upper cover shell 1411 and the lower shell 1412 by deposition or solution method, or a separate closed shell layer.

In the preferred embodiment of the invention, the electrolyte isolation layer 147 is a film of 300-500 um thickness. The thickness of the electrolyte isolation layer 147 is too thin, and the electrolyte isolation layer 147 will be infiltrated and softened by the electrolyte. After a long time, it will lead to the aging of the film material, and the thickness is too thick. The electrolyte isolation layer 147 will occupy the interior space of the cavity. In a preferred embodiment of the invention, the thickness of the electrolyte isolation layer 147 is 400 um.

In the embodiment of the invention, diaphragm 142, electrolyte 143, anode plate 144, cathode plate 145 and conductive strip 146 are also arranged in the battery cavity 14. The anode plate 144 and cathode plate 145 are infiltrated in electrolyte 143 and separated by diaphragm 142.

In an embodiment of the invention, the diaphragm 142, the anode plate 144 and the cathode plate 145 are wound structures, and the diaphragm 142 is located between the anode plate 144 and the cathode plate 145. Referring to FIG. 2, in the battery cavity profile, the two ends of the diaphragm 142 are respectively against the electrolyte isolation layer 147 to completely isolate the cathode plate 145 and the anode plate 144.

In other embodiments of the invention, the diaphragm 142, the anode plate 144 and the cathode plate 145 may also be laminated.

In an embodiment of the invention, the solute of electrolyte 143 is lithium salt, such as one of lithium perchlorate ($LiClO_4$), lithium hexafluorophosphate ($LiPF_6$), lithium tetrafluoroborate ($LiBF_4$). The solvent is one of vinyl carbonate, propylene carbonate, diethyl carbonate, dimethyl carbonate, methyl carbonate, phosphorus pentafluoride, hydrofluoric acid, ether, ethylene carbonate, propylene carbonate, diethyl carbonate. In the preferred embodiment of the invention, the solvent is organic solvent, such as ether, ethylene carbonate, propylene carbonate, diethyl carbonate.

In an embodiment of the invention, the main material of the anode plate 144 is manganese dioxide and is prepared by the following process:

(1) The electrolytic manganese dioxide, conductive agent and binder were screened through a screen or air classifier, select the particle size less than 200 um electrolytic manganese dioxide particles, placed in the quartz boat, heat treatment was carried out in the sintering furnace and the temperature was heated to 200° C. for 4 h. The purpose of this step is to make electrolytic manganese dioxide lose part of binding water, X-ray diffraction peak shift, crystal plane spacing decrease, Mn—O bond force increase, so as to enhance the discharge capacity of electrolytic manganese dioxide.

(2) After the electrolytic manganese dioxide in step (1) is cooled to below 60° C., an electronic balance is used to weigh 9 g electrolytic manganese dioxide, 0.5 g conductive agent with particle size less than 200 μm, and 0.5 g binder with particle size less than 200 um, put them in the grinding dish, fully stir and mix, then grind manually or electrically to get 10 g grinding mixture. And allows the grinding mixture to pass through a screen of 300 mesh (size 48 um). The purpose of this step is to ensure the uniformity of the mixture and avoid the phenomenon of uneven dispersion of conductive agent and binder.

In other embodiments of the invention, the mass proportion of electrolytic manganese dioxide, conductive agent and binder is not limited to the above proportion, and the mass proportion can be 80%-96%, 2%-10% and 2%-10% respectively.

In preferred embodiments of the invention, the conductive agent may be one or more of conductive carbon black, graphite, super P or carbon nanotubes.

In preferred embodiments of the invention, the binder may be one or more of PVDF (polyvinylidene fluoride), polytetrafluoroethylene, or sodium polyacrylate.

(3) The grinding mixture is placed in a vacuum drying oven and heated to 65° C. for 5 h to dry the moisture that may exist in the mixture to ensure that the sample is dry and the positive mixture is obtained.

(4) Drop 10 g of NMP(N-methyl-pyrrolidone) solvent in a dry glass bottle, and then slowly add the positive mixture to the glass bottle, and stir with a magnetic stirrer for 3 h, to ensure that the mixture is uniform, to get a solid content of 50% anode paste. The purpose of this step is to ensure that the components of the anode paste dispersed evenly, and the solid content and the viscosity of the anode paste has a certain relationship, 50% solid content of the anode paste viscosity is better, coated on the base after the film effect is better, can reduce the phenomenon of powder or rupture.

(5) The use of plate coating machine will be positive paste coated on the surface of the base, the conductive layer, and then the conductive layer and the base in a vacuum drying oven baking, heating to 110° C., for 12 h, to ensure that the water is completely dried.

In the preferred embodiment of the invention, the base material is one of aluminum foil or foam nickel mesh, and the thickness is 12-18 um.

In a preferred embodiment of the invention, the base material is aluminum foil with a thickness of 15 um.

(6) The use of electric vertical roller press on the conductive layer and the base of the roll, can make the overall thickness of the conductive layer and the base down to 180-220 um, get the anode plate finished product. By adjusting the working parameters of the coating machine and the roller press, the thickness of the anode plate can be controlled to ensure that the electrode plate can have a relatively perfect conductive network on the premise of higher compaction density, so as to meet the working requirements of large current pulse discharge.

Figure 3:
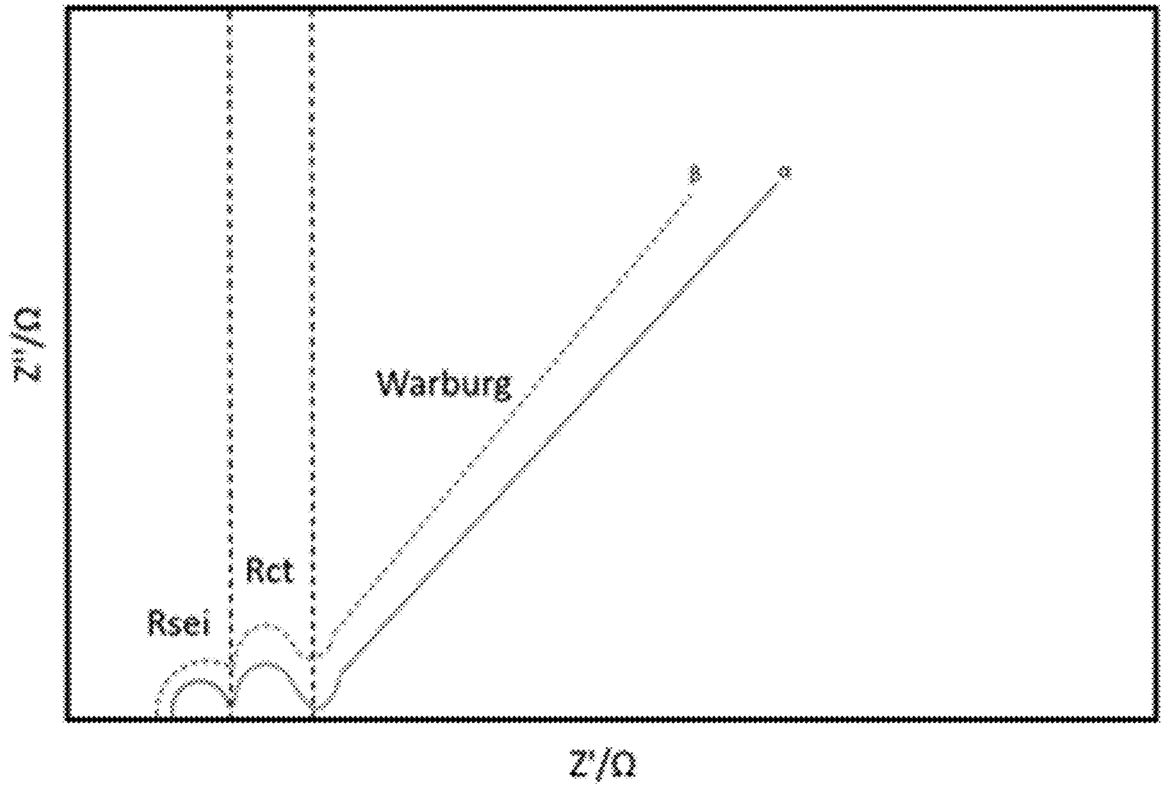
FIG. 3 is a contrast diagram of electrochemical impedance spectra of anode plate according to an embodiment of the invention.

FIG. 3 is the contrast diagram of electrochemical impedance spectrum. The solid line α is the electrochemical impedance curve of the anode plate α processed according to the process steps of the embodiment of the present invention (coating method combining dry and wet mixture), and the dotted line β is the electrochemical impedance curve of the anode plate β processed by the prior art process steps (tablet paste method). Can be seen from the diagram, in the stage of Rsei, the curvature of the solid line α is smaller than that of the dotted line β, indicating that the polarization degree of the anode plate α is smaller than that of the anode plate β, and the wetness of the electrolyte of the anode plate α is better than that of the anode plate β, so when large current pulse discharge, the resistance of a is smaller than that of β, which improves the discharge capacity of the battery. Secondly, in the stage of Rct, the curvature of the solid line α is still smaller than the curvature of the dotted line β, indicating that the resistance of the anode plate α is smaller than that of the anode plate β. This is because the porosity of the anode plate α is larger than that of the anode plate β in the same environment in the battery. The anode plate α can accommodate more and higher concentration of electrolyte. The discharge capacity of the battery under large current pulse is further improved.

In an embodiment of the invention, the cathode plate 145 is mainly lithium base material.

In other embodiment of the invention, the anode plate 144 can also be lithium manganese acid, lithium cobalt acid, lithium iron phosphate and other lithium containing compounds, and corresponding the cathode plate 145 is graphite.

In embodiments of the invention, the material of the diaphragm 142 is PE (polyethylene) or PP (polypropylene), which can be a single layer of PE or PP or three layers of PE or PP.

In the embodiment of the invention, one end A of the conductive strip 146 is fixedly connected with the anode plate 144 or the cathode plate 145, and the other end B of the conductive strip 146 is electrically connected with the circuit board 13 through the electrolyte isolation layer 147 and the lower shell 1412. The lower shell 1412 is provided with a groove or through-hole 1461 for the conductive strip 146 to pass through. In the preferred embodiment of the invention, the end A is fixedly connected with anode plate 144 or cathode plate 145 by means of solder or solder paste.

In an embodiment of the invention, the conductive strip 146 connected with the anode plate 144 is made of aluminum, and the conductive strip 146 connected with the cathode plate 145 is made of nickel or copper plated nickel.

In the embodiment of the invention, the connection between the upper cover shell 1411 and the lower shell 1412, and the connection between the conductive strip 146 and the lower shell 1412 are coated with insulating sealant. On the one hand, the insulating sealant is used to fix the upper cover shell 1411 and the lower shell 1412, and the conductive strip 146 and the lower shell 1412. On the other hand, the insulating sealant prevents electrolyte 143 from leaking to the outside world, causing unnecessary pollution.

In the preferred embodiment of the invention, the insulating sealant is one of hot melt adhesive or silica gel, both of which have high thermoplastic and adhesive force, and the hot melt adhesive also contributes to the self-thermal runaway management of the battery.

Specifically, in the preferred embodiment of the invention, when the lower shell 1412 and the lower outer shell 12 and the upper cover shell 1411 and the upper outer shell 11 are injection molded in one body at the same time, the processing process of battery cavity 14 is as follows:

(1) Coat the inside of the upper cover shell 1411 and the lower shell 1412 with PET or TPE material with a thickness of 300-500 um. Put it in a constant temperature oven and set the temperature 60-85° C. until the coating material is completely dry;

(2) The battery (comprising cathode plate 145, conductive strip 146, diaphragm 142, anode plate 144) is placed in the lower shell 1412, one end of the conductive strip 146 is fixed on the lower shell 1412 by insulating sealant, while the other end of the conductive strip 146 is fixedly connected with the anode plate and cathode plate by soldering or solder paste;

(3) The lower shell 1412 is placed in a static position, and electrolyte 143 is injected into the lower shell 1412 with a pipette gun, and then moved to the vacuum position in the transition chamber to ensure that the electrolyte is fully infiltrated into the anode plate and cathode plate, so as to improve the electrochemical performance of the battery cavity;

(4) After the lower shell 1412 is left standing, apply insulating sealant at its connection with the upper cover shell 1411, and then cover the upper cover shell 1411 to maintain the tightness and obtain a complete battery cavity.

Continue by referring to FIGS. 1*a* and 1*b*. In an embodiment of the invention, the sensor 15 comprises an external part 151 and an internal part 152. The external part 151 is tiled on the inside of the upper outer shell 11 to reduce the height of the sensor and thus the thickness of the analyte detection device. The internal part 152 bends with respect to the external part 151 and passes through the through hole 111 on the upper outer shell 11 to the outside of the upper outer shell 11. In the preferred embodiment of the invention, the internal part 152 is bent at 900 relative to the external part 151.

In the embodiment of the invention, the internal part 152 is inserted under the user's skin to obtain the analyte parameter information, and the external part 151 is electrically connected with the circuit board 13 to send the analyte parameter information to external equipment through the transmitter antenna 131 on the circuit board. In an embodiment of the invention, the transmitter antenna 131 communicates with external equipment.

Figure 4A:
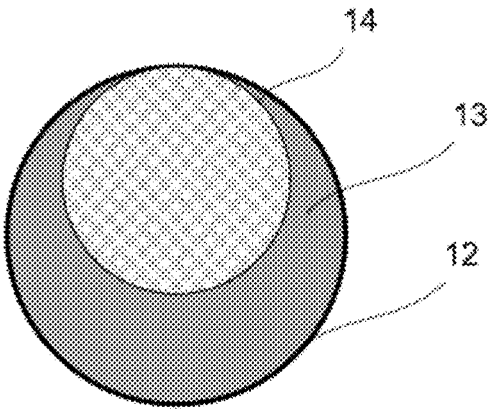
FIGS. 4*a*-4*c* are schematic diagrams of circuit board shapes according to the first embodiment of the present invention.
Figure 4B:
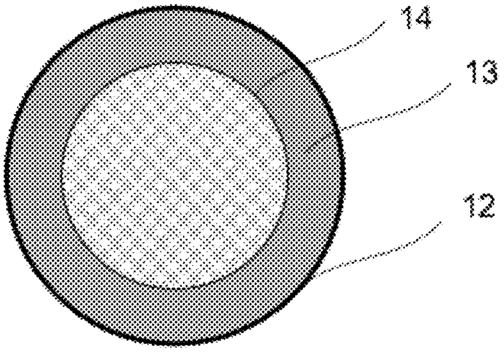
Figure 4C:
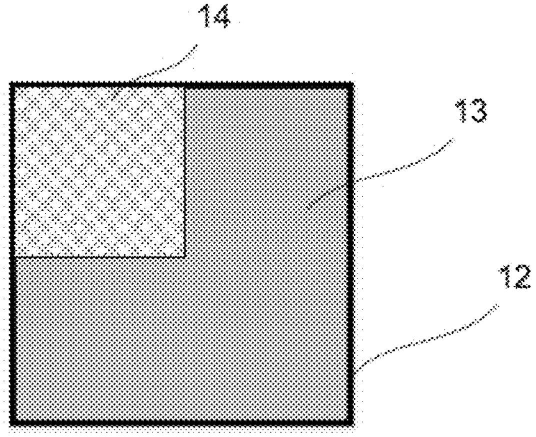

FIG. 4*a*-FIG. 4*c* is a schematic diagram of the circuit board.

In an embodiment of the invention, the shape of circuit board 13 is adapted to the shape of the lower outer shell 12 and the lower shell 1412. Here, "adapted" means that the shape of circuit board 13 is designed to fill the remaining available space inside the lower outer shell 12 on the premise that the lower shell 1412 has occupied the given space. For example, the lower outer shell 12 is round, the lower shell 1412 is eccentrically round with the lower outer shell 12, the circuit board 13 can be designed as crescent. When the lower outer shell 12 is round and the lower outer shell 1412 is concentric round, the circuit board 13 can be designed as a circular ring. When the lower outer shell 12 is square and the lower shell 1412 is eccentric square of the lower outer shell 12, the circuit board 13 can be designed as "7" shape. In addition to the above possible shapes of circuit board 13, circuit board 13 can be designed in any other shape, provided that it fills the interior space of the lower outer shell 12.

In an embodiment of the invention, a sticky patch (not shown in the figure) is also arranged on the outer side of the upper outer shell 11, which is used to fix the analyte detection device on the user's skin surface.

Second Embodiment

Figure 5A:
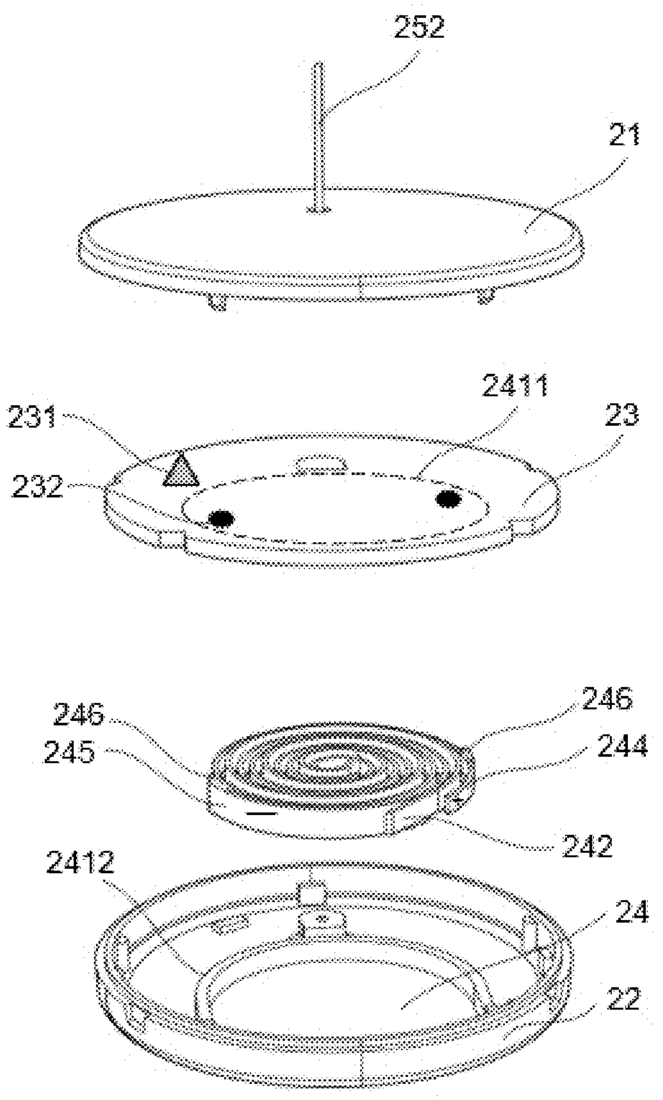
FIG. 5*a* is the explosive structure diagram of an analyte detection device with battery and shell integrated according to the second embodiment of the invention.

FIG. 5*a* is the explosive structure diagram of the integrated analyte detection device with battery and shell integrated in the second embodiment of the invention.

Figure 5B:
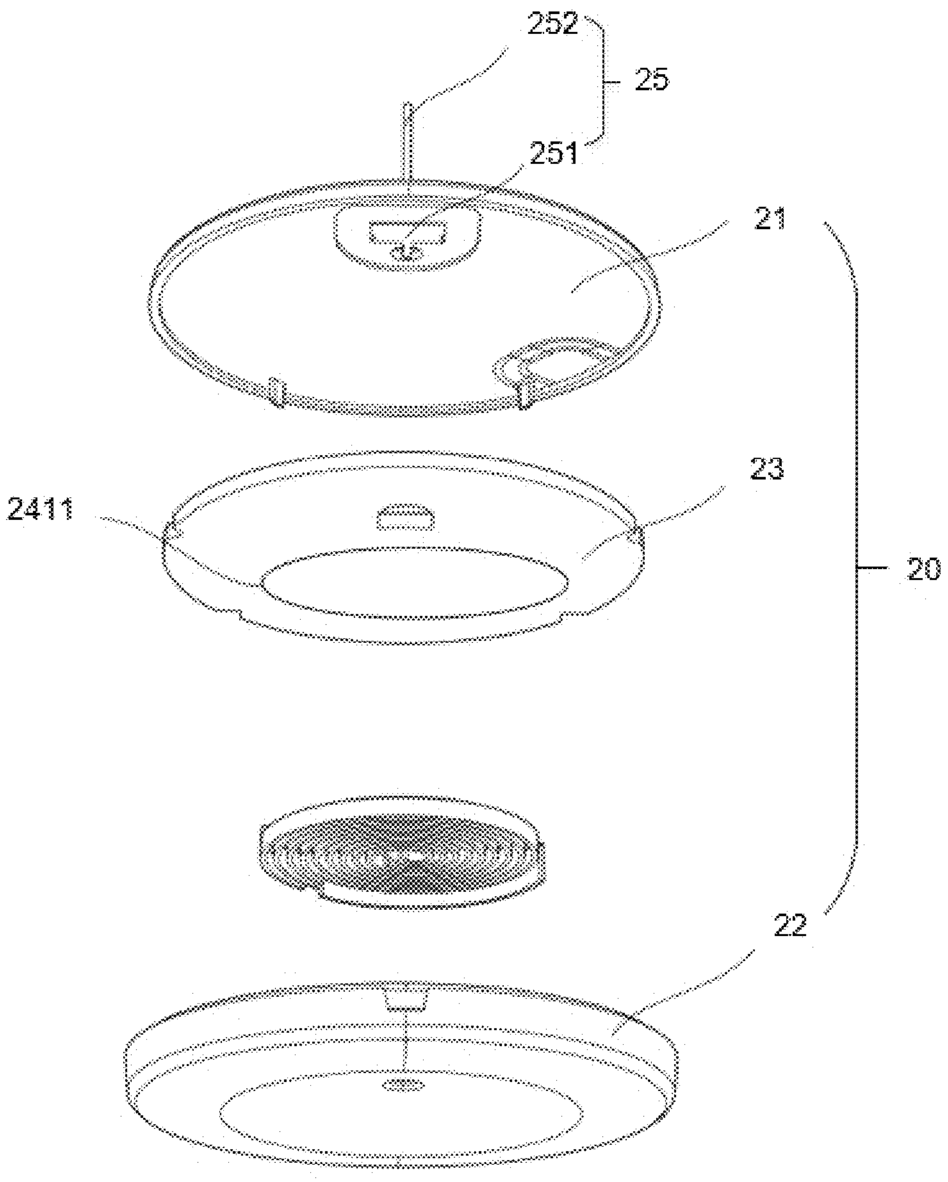
FIG. 5*b* is the other direction explosive structure diagram of an analyte detection device with battery and shell integrated according to the second embodiment of the invention.

FIG. 5*b* is the other direction explosive structure diagram of the analyte detection device with battery and shell integrated in the second embodiment of the invention.

Figure 5C:
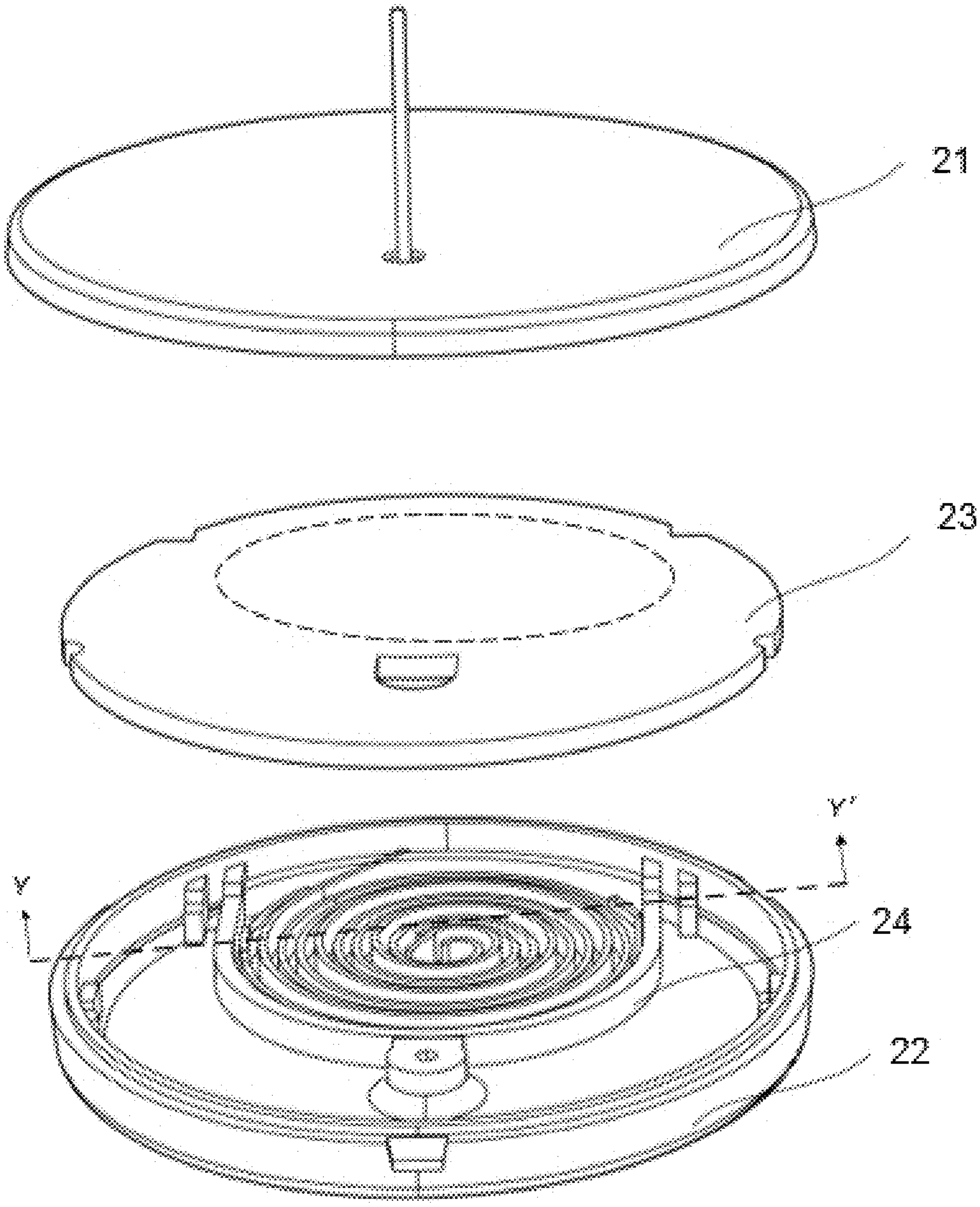
FIG. 5*c* is a schematic diagram of the electrode plate located in the battery cavity according to the second embodiment of the invention.

FIG. 5*c* is a schematic diagram of the structure of the electrode plate in the battery cavity of the second embodiment of the invention.

Figure 6:
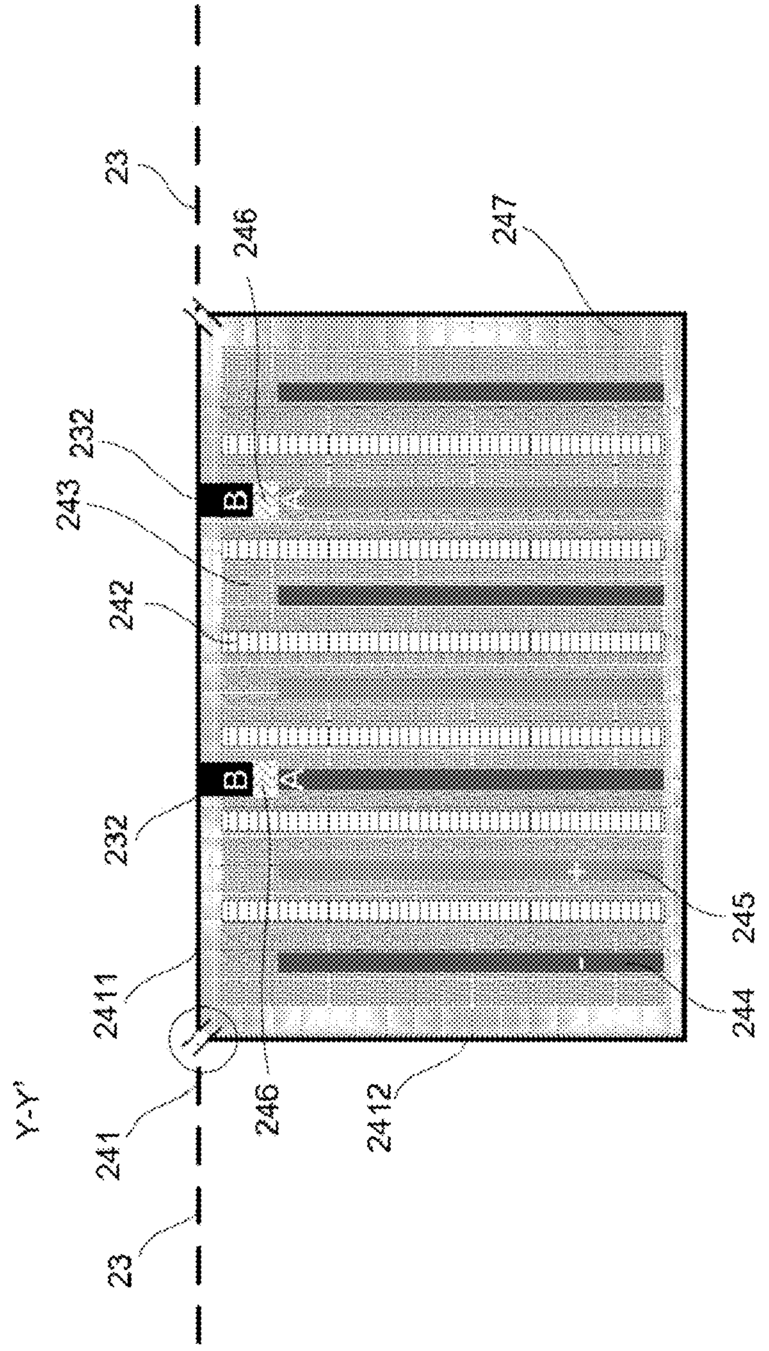
FIG. 6 is a schematic diagram of the Y-Y' section structure of the battery cavity according to the second embodiment of the invention.

FIG. 6 is a schematic diagram of Y-Y' section structure of the battery cavity in the second embodiment of the invention.

Combine with reference FIG. 1*a*, FIG. 1*b* and FIG. 2. The detection device comprises the outer shell 20, the circuit board 23, the battery cavity 24 and the sensor 25. Outer shell 20 comprises an upper outer shell 21 and a lower outer shell 22, circuit board 23 and battery cavity 24 are arranged on the lower outer shell 22, and the sensor 25 is arranged on the upper outer shell 21.

In the embodiment of the invention, the outer shell 20 of the detection device adopts a material of PE, PP, HDPE, PVC, ABS, PMMA, PC, PPS or PU, whose low density can reduce the weight of the detection device and improve the user experience.

In an embodiment of the invention, the cavity shell 241 of battery cavity 24 comprises an upper cover shell 2411 and a lower shell 2412. The upper cover body 2411 is a part of the circuit board 23, forming the structure of the upper cover body 2411 and the circuit board 23 integration.

In other embodiment of the invention, the bottom of the lower shell 2412 is a part of the lower outer shell 22, and the side wall of the lower shell 2412 is raised in the lower outer shell 22 and is oriented towards the upper outer shell 21, forming a structure of the lower shell 2412 and the lower outer shell 22 integration. Preferably, the lower shell 2412 is of the same material as the lower outer shell 22, which is convenient for integrated injection molding during processing.

In the embodiment of the invention, circuit board 23 is made of plastic material. For the upper cover shell 2411 and the lower shell 2412 are made of plastic, they are easy to be corroded by electrolyte, an electrolyte isolation layer 247 is also required to be set on the inner side of the upper cover shell 2411 and the lower shell 2412.

In the embodiment of the invention, the material of the electrolyte isolation layer 247 is one of TPE or PET (polyethylene terephthalate). TPE is a thermoplastic elastomer material with strong processability. PET can be used as the container of electrolyte, which can effectively isolate the corrosion of electrolyte to the cavity shell and circuit devices.

In embodiments of the present invention, the electrolyte isolation layer 247 may be either a film coated on the inner side of the upper cover shell2411 and the lower shell 2412 by deposition or solution method, or a separate closed shell layer.

In the preferred embodiment of the invention, the electrolyte isolation layer 247 is a film of 300-500 um thickness. The thickness of the electrolyte isolation layer 247 is too thin, and the electrolyte isolation layer 247 will be infiltrated and softened by the electrolyte. After a long time, it will lead to the aging of the film material, and the thickness is too thick. The electrolyte isolation layer 247 will occupy the interior space of the cavity. In a preferred embodiment of the invention, the thickness of the electrolyte isolation layer 247 is 400 um.

In the embodiment of the invention, diaphragm 242, electrolyte 243, anode plate 244, cathode plate 245 and conductive strip 246 are also arranged in the battery cavity 24. The anode plate 244 and cathode plate 245 are infiltrated in electrolyte 243 and separated by diaphragm 242.

In an embodiment of the invention, the diaphragm 242, the anode plate 244 and the cathode plate 245 are wound structures, and the diaphragm 242 is located between the anode plate 244 and the cathode plate 245. Referring to FIG. 6, in the battery cavity profile, the two ends of the diaphragm 242 are respectively against the electrolyte isolation layer 247 to completely isolate the cathode plate 245 and the anode plate 244.

In other embodiments of the invention, the diaphragm 242, the anode plate 244 and the cathode plate 245 may also be laminated.

In an embodiment of the invention, the solute of electrolyte 243 is lithium salt, such as one of lithium perchlorate ($LiClO_4$), lithium hexafluorophosphate ($LiPF_6$), lithium tetrafluoroborate ($LiBF_4$). The solvent is one of vinyl carbonate, propylene carbonate, diethyl carbonate, dimethyl carbonate, methyl carbonate, phosphorus pentafluoride, hydrofluoric acid, ether, ethylene carbonate, propylene carbonate, diethyl carbonate. In the preferred embodiment of the invention, the solvent is organic solvent, such as ether, ethylene carbonate, propylene carbonate, diethyl carbonate.

In an embodiment of the invention, the main material of the anode plate 244 is manganese dioxide and is prepared by the following process:

(1) The electrolytic manganese dioxide, conductive agent and binder were screened through a screen or air classifier, select the particle size less than 200 um electrolytic manganese dioxide particles, placed in the quartz boat, heat treatment was carried out in the sintering furnace and the temperature was heated to 200° C. for 4 h. The purpose of this step is to make electrolytic manganese dioxide lose part of binding water, X-ray diffraction peak shift, crystal plane spacing decrease, Mn—O bond force increase, so as to enhance the discharge capacity of electrolytic manganese dioxide.

(2) After the electrolytic manganese dioxide in step (1) is cooled to below 60° C., an electronic balance is used to weigh 9 g electrolytic manganese dioxide, 0.5 g conductive agent with particle size less than 200 μm, and 0.5 g binder with particle size less than 200 um, put them in the grinding dish, fully stir and mix, then grind manually or electrically to get 10 g grinding mixture. And allows the grinding mixture to pass through a (2) ... screen of 300 mesh (size 48 um). The purpose of this step is to ensure the uniformity of the mixture and avoid the phenomenon of uneven dispersion of conductive agent and binder.

In other embodiments of the invention, the mass proportion of electrolytic manganese dioxide, conductive agent and binder is not limited to the above proportion, and the mass proportion can be 80%-96%, 2%-10% and 2%-10% respectively.

In preferred embodiments of the invention, the conductive agent may be one or more of conductive carbon black, graphite, super P or carbon nanotubes.

In preferred embodiments of the invention, the binder may be one or more of PVDF (polyvinylidene fluoride), polytetrafluoroethylene, or sodium polyacrylate.

(3) The grinding mixture is placed in a vacuum drying oven and heated to 65° C. for 5 h to dry the moisture that may exist in the mixture to ensure that the sample is dry and the positive mixture is obtained.

(4) Drop 10 g of NMP(N-methyl-pyrrolidone) solvent in a dry glass bottle, and then slowly add the positive mixture to the glass bottle, and stir with a magnetic stirrer for 3 h, to ensure that the mixture is uniform, to get a solid content of 50% anode paste. The purpose of this step is to ensure that the components of the anode paste dispersed evenly, and the solid content and the viscosity of the anode paste has a certain relationship, 50% solid content of the anode paste viscosity is better, coated on the base after the film effect is better, can reduce the phenomenon of powder or rupture.

(5) The use of plate coating machine will be positive paste coated on the surface of the base, the conductive layer, and then the conductive layer and the base in a vacuum drying oven baking, heating to 110° C., for 12 h, to ensure that the water is completely dried.

In the preferred embodiment of the invention, the base material is one of aluminum foil or foam nickel mesh, and the thickness is 12-18 um.

In a preferred embodiment of the invention, the base material is aluminum foil with a thickness of 15 um.

(6) The use of electric vertical roller press on the conductive layer and the base of the roll, can make the overall thickness of the conductive layer and the base down to 180-220 um, get the anode plate finished product. By adjusting the working parameters of the coating machine and the roller press, the thickness of the anode plate can be controlled to ensure that the electrode plate can have a relatively perfect conductive network on the premise of higher compaction density, so as to meet the working requirements of large current pulse discharge.

According to FIG. 3, the effect of anode plate 244 obtained by the above processing process is consistent with embodiment 1 of the invention and will not be described here.

In an embodiment of the invention, the cathode plate 245 is mainly lithium base material.

In other embodiment of the invention, the anode plate 244 can also be lithium manganese acid, lithium cobalt acid, lithium iron phosphate and other lithium containing compounds, and corresponding the cathode plate 245 is graphite.

In embodiments of the invention, the material of the diaphragm 242 is PE (polyethylene) or PP (polypropylene), which can be a single layer of PE or PP or three layers of PE or PP.

In the embodiment of the invention, one end A of the conductive strip 246 is fixedly connected with the anode plate 244 or the cathode plate 245, and the other end B of the conductive strip 246 is electrically connected with the power electrode 232 of the circuit board 23.

In an embodiment of the invention, the end B of the conductive strip 246 is fixedly connected with the power electrode 232 by means of solder or solder paste.

In an embodiment of the invention, the power electrode 232 is a metal contact protruding from the circuit board 23 and the electrolyte isolation layer 247, and the connection between the power electrode 232 and the circuit board 23 is covered by the electrolyte isolation layer 247 to prevent electrolyte 243 from leaking.

In the preferred embodiment of the invention, the end A is fixedly connected with anode plate 244 or cathode plate 245 by means of solder or solder paste.

In an embodiment of the invention, the conductive strip 246 connected to the anode plate 244 is made of aluminum, and the conductive strip 246 connected to the cathode plate 245 is made of nickel or copper-plated nickel.

In the embodiment of the invention, the connection between the upper cover shell 2411 and the lower shell 2412, and the connection between the conductive strip 246 and the lower shell 2412 are coated with insulating sealant. On the one hand, the insulating sealant is used to fix the upper cover shell 2411 and the lower shell 2412, and the conductive strip 246 and the lower shell 2412. On the other hand, the insulating sealant prevents electrolyte 243 from leaking to the outside world, causing unnecessary pollution.

In the preferred embodiment of the invention, the insulating sealant is one of hot melt adhesive or silica gel, both of which have high thermoplastic and adhesive force, and the hot melt adhesive also contributes to the self-thermal runaway management of the battery.

Specifically, in the preferred embodiment of the invention, when the lower shell 2412 and the lower outer shell 22 and/or the upper cover shell 2411 and the upper outer shell 21 are injection molded in one body at the same time, the processing process of battery cavity 24 is as follows:

(1) Coat the inside of the upper cover shell 2411 and the lower shell 2412 with PET or TPE material with a thickness of 300-500 um. Put it in a constant temperature oven and set the temperature 60-85° C. until the coating material is completely dry;

(2) The battery (comprising cathode plate 245, conductive strip 246, diaphragm 242, anode plate 244) is placed in the lower shell 2412, one end of the conductive sheet 246 is connected with the anode plate and cathode plate by solder or solder paste;

(3) The lower shell 2412 is placed in a static position, and electrolyte 243 is injected into the lower shell 2412 with a pipette gun, and then moved to the vacuum position in the transition chamber to ensure that the electrolyte is fully infiltrated into the anode plate and cathode plate, so as to improve the electrochemical performance of the battery cavity;

(4) After the lower shell 2412 is left standing, the upper cover body 2411 (circuit board 23) is closed. At this time, the other end of the conductive sheet 246 is connected with the power electrode 232 of circuit board 23 through tin welding or solder paste.

(5) Insulating sealant is applied to the joint of the lower shell 2412 and the upper cover shell 2411 to maintain the sealing and obtain a complete battery cavity.

Continue by referring to FIGS. 5*a* and 5*b*. In an embodiment of the invention, the sensor 25 comprises an external part 251 and an internal part 252. The external part 251 is tiled on the inside of the upper outer shell 11 to reduce the height of the sensor and thus the thickness of the analyte detection device. The internal part 252 bends with respect to the external part 251 and passes through the through hole 211 on the upper outer shell 21 to the outside of the upper outer shell 21. In the preferred embodiment of the invention, the internal part 252 is bent at 900 relative to the external part 251.

In the embodiment of the invention, the internal part 252 is inserted under the user's skin to obtain the analyte parameter information, and the external part 251 is electrically connected with the circuit board 23 to send the analyte parameter information to external equipment through the transmitter antenna 231 on the circuit board. In an embodiment of the invention, the transmitter antenna 231 communicates with external equipment.

To sum up, the invention provides an analyte detection device with battery and shell integrated. The battery cavity is installed in the outer shell, the battery cavity comprises the cavity shell, the diaphragm, the electrolyte, the anode plate, cathode plate and the conductive strip, the electrolyte isolation layer is also arranged inside the cavity shell, to form the structure of battery and circuit board integration, the shape and size of the analyte detection device are no longer limited by the shape and size of the shell of the button battery, and the shape and size of the battery cavity can be optimized according to the miniaturization design requirements of the analyte detection device to improve user experience.

Although some specific embodiments of the present invention have been elaborated by examples, those skilled in the field should understand that the above examples are intended only to illustrate and not to limit the scope of the present invention. Those skilled in the field should understand that modifications to the above embodiments may be made without departing from the scope and spirit of the invention. The scope of the invention is limited by the attached claims.

The invention claimed is:

1. An analyte detection device with battery and shell integrated, which comprises:

an outer shell comprising an upper outer shell and a lower outer shell, wherein a sensor is arranged on the upper outer shell;

a circuit board arranged inside the lower outer shell and provided with a transmitter antenna, wherein the transmitter antenna is used for communicating with external devices; and a battery cavity arranged inside the lower outer shell and comprising a cavity shell, a diaphragm, an electrolyte, an anode plate, a cathode plate and a conductive strip, wherein the cavity shell comprises an upper cover shell and a lower shell, the upper cover shell is integrated with the circuit board to form a part of the circuit board, and the circuit board forms a sealing cover with the lower shell of the battery cavity for containing the electrolyte.

2. The analyte detection device with battery and shell integrated of claim 1, wherein the lower shell is integrated with the lower outer shell.

3. The analyte detection device with battery and shell integrated of claim 1, wherein an electrolyte isolation layer is arranged inside the cavity shell.

4. The analyte detection device with battery and shell integrated of claim 3, wherein the electrolyte isolation layer is made of TPE or PET material.

5. The analyte detection device with battery and shell integrated of claim 4, wherein the electrolyte isolation layer is a thin film coated on an inner wall of the cavity shell.

6. The analyte detection device with battery and shell integrated of claim 5, wherein a thickness of the electrolyte isolation layer is 300-500 um.

7. The analyte detection device with battery and shell integrated of claim 4, wherein the electrolyte isolation layer is a closed shell independent of the cavity shell.

8. The analyte detection device with battery and shell integrated of claim 1, wherein the circuit board also comprises a power electrode, a first end of the conductive strip is fixedly connected with the anode plate or the cathode plate, and a second end of the conductive strip is electrically connected with the power electrode.

9. The analyte detection device with battery and shell integrated of claim 8, wherein a connection between the upper cover shell and the lower shell is coated with insulating sealant.

10. The analyte detection device with battery and shell integrated of claim 9, wherein the insulation sealant is one of hot melt adhesive and silica gel.

11. The analyte detection device with battery and shell integrated of claim 8, wherein the second end of the conductive strip is fixedly connected with the power electrode through solder or solder paste.

12. The analyte detection device with battery and shell integrated of claim 1, wherein a material of the upper outer shell or the lower outer shell is one of PE, PP, HDPE, PVC, ABS, PMMA, PC, PPS and PU.

13. The analyte detection device with battery and shell integrated of claim 1, wherein the sensor comprises an internal part and an external part, and the internal part is bent with the external part.

14. The analyte detection device with battery and shell integrated of claim 13, wherein the external part is tiled in the upper cover shell, and the internal part passes through the upper outer shell to outside.

* * * * *